US009073962B2

(12) United States Patent
Fracchia et al.

(10) Patent No.: US 9,073,962 B2
(45) Date of Patent: Jul. 7, 2015

(54) METHODS OF SERIAL ASSEMBLY OF DNA BRICKS INTO LARGER STRUCTURES

(71) Applicants: Charles Fracchia, Cambridge, MA (US); Neil Gershenfeld, Cambridge, MA (US); Kenneth Cheung, Freehold, NJ (US)

(72) Inventors: Charles Fracchia, Cambridge, MA (US); Neil Gershenfeld, Cambridge, MA (US); Kenneth Cheung, Freehold, NJ (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/941,405

(22) Filed: Jul. 12, 2013

(65) Prior Publication Data

US 2014/0018441 A1 Jan. 16, 2014

Related U.S. Application Data

(60) Provisional application No. 61/670,606, filed on Jul. 12, 2012.

(51) Int. Cl.
*C07H 21/04* (2006.01)

(52) U.S. Cl.
CPC ..................................... *C07H 21/04* (2013.01)

(58) Field of Classification Search
CPC ................................ C07H 21/04; C07H 21/00
See application file for complete search history.

(56) References Cited

U.S. PATENT DOCUMENTS

| 2009/0239293 A1 | 9/2009 | Sandell |
| 2010/0009868 A1 | 1/2010 | Yan et al. |
| 2012/0022243 A1 | 1/2012 | Yin et al. |

FOREIGN PATENT DOCUMENTS

| WO | 2009043184 A1 | 4/2009 |
| WO | WO2013022694 A1 | 2/2013 |

OTHER PUBLICATIONS

Dill, et al. (2008) "The Protein Folding Problem", Annual Review of Biophysics, 37: 289-316.*

International Search Report and Written Opinion of the International Searching Authority, dated Dec. 16, 2013, PCT/US2013/050394.
Hung, A., et al., 2010, Recent Advances in DNA-based directed assembly on surfaces. Nanoscale, 2010, 2, pp. 2530-2537, first published online Sep. 13, 2010, Royal Society of Chemistry.
Weizmann, Y., et al., 2008, A polycatenated DNA scaffold for the one-step assembly of hierarchical nanostructures. Proceedings of the National Academy of Sciences of the United States of America, PNAS, Apr. 8, 2008, vol. 105, No. 14, pp. 5289-5294, Apr. 8, 2008.
Cheung, K., et al., 2011, Programmable Assembly With Universally Foldable Strings (Moteins). IEEE Transactions on Robotics, vol. 27, Issue 4, pp. 718-729, Jun. 2011, IEEE Robotics and Automation Society.
Ke, Y., et al., 2012, Three-Dimensional Structures Self-Assembled from DNA Bricks. Science , Nov. 30, 2012, vol. 338 No. 6111, pp. 1177-1183, American Association for the Advancement of Science, New York, NY 2012.
Lin, C., et al., 2006, DNA tile based self-assembly: building complex nanoarchitectures. Chemphyschem, Aug. 11, 2006, 7(8), pp. 1641-1647.
Park, S., et al., 2006, Finite-Size, Fully Addressable DNA Tile Lattices Formed by Hierarchical Assembly Procedures. Angewandte Chemie International Edition, vol. 45, Issue 5, pp. 735-739, Jan. 23, 2006.
Rothemund, P., 2006, Folding DNA to create nanoscale shapes and patterns. Nature, vol. 440, pp. 297-302, Mar. 16, 2006.
Stein, I., et al., 2011, Single-Molecule Four-Color FRET Visualizes Energy-Transfer Paths on DNA Origami. J. Am. Chem. Soc., 2011, 133 (12), pp. 4193-4195, Jan. 20, 2011.
Wei, B., et al. Complex shapes self-assembled from single-stranded DNA tiles. Nature vol. 485, pp. 623-626, May 31, 2012.

* cited by examiner

*Primary Examiner* — Robert M Kelly
(74) *Attorney, Agent, or Firm* — Stephen R. Otis

(57) ABSTRACT

In exemplary implementations of this invention, hierarchical, nanometer-precise assembly is performed: A first structural unit is attached to a solid substrate in a first fluidic flow. A second structural unit is attached to the first structural unit in a second fluidic flow, a third structural unit is attached to the second structural unit in a third fluidic flow, and so on, until a target structure comprising the structural units is assembled. The first, second, third and so on fluidic flows are separate and occur in order in a temporal sequence. During the temporal sequence, a specific permutation of nucleobases is used repeatedly, in separate fluidic flows which occur at different times, to form multiple attachments between structural units in an assembly. The assembled target structure is removed from the solid substrate. Attachments between the structural units may be formed by nucleobase pairing.

13 Claims, 13 Drawing Sheets

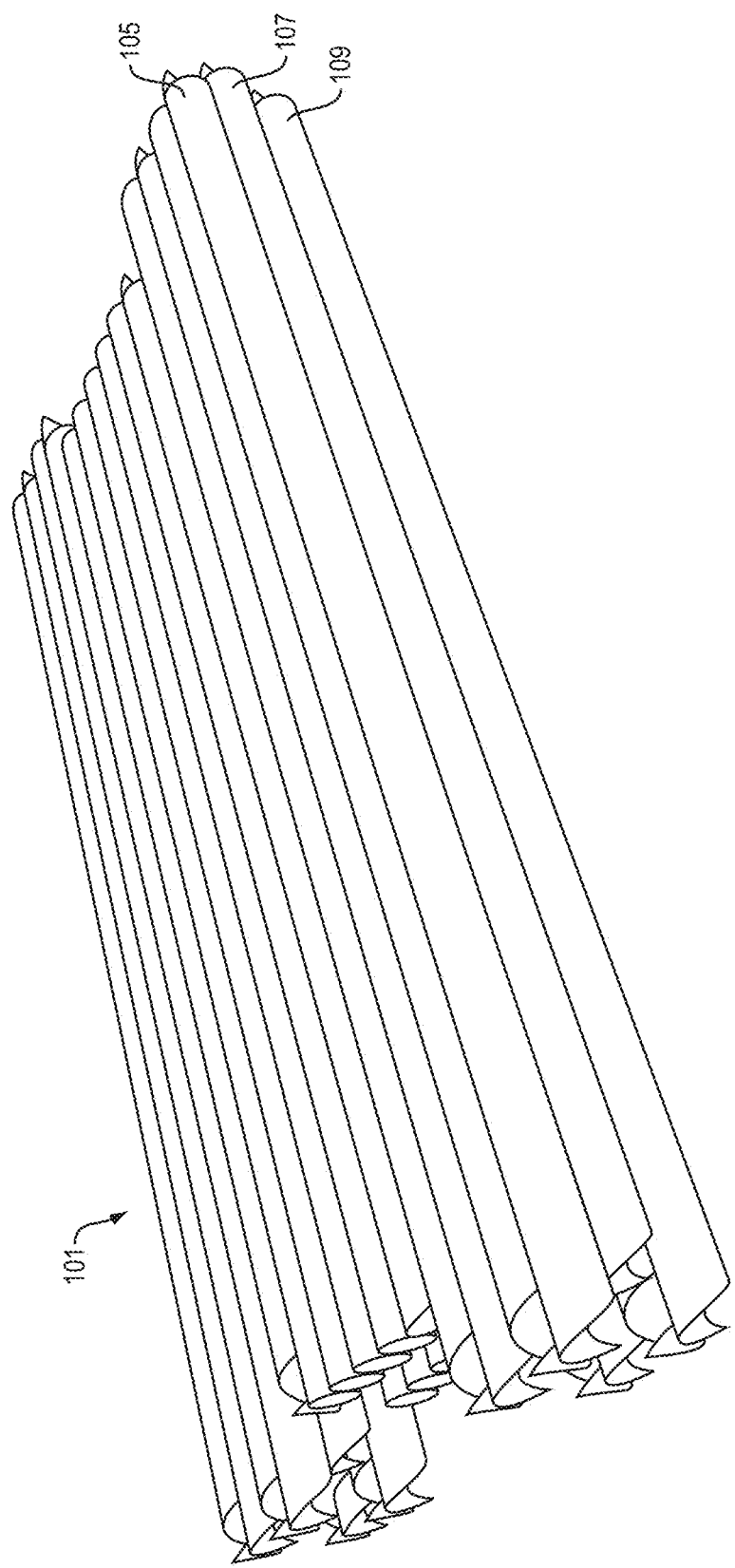

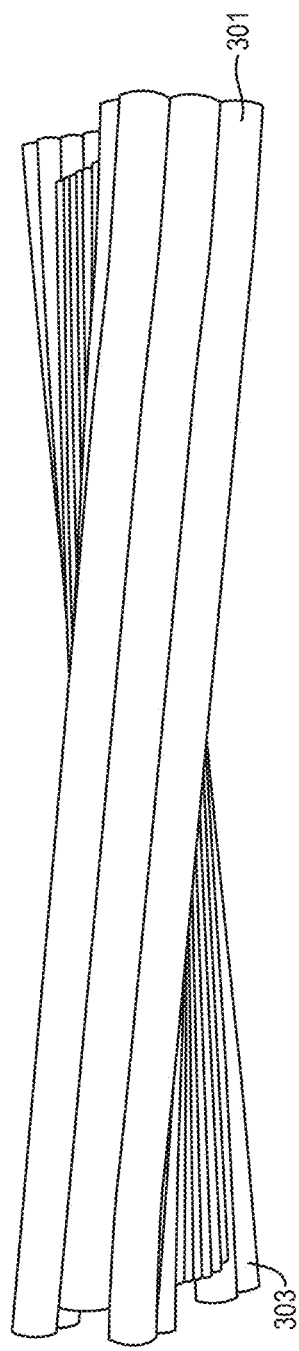
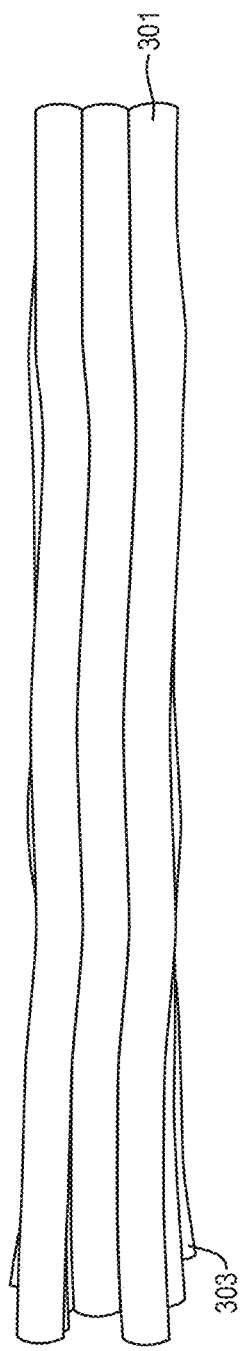

METHODS OF SERIAL ASSEMBLY OF DNA BRICKS INTO LARGER STRUCTURES

RELATED APPLICATIONS

This application is a non-provisional of, and claims the benefit of the filing date of, U.S. Provisional Application No. 61670606, filed Jul. 12, 2012, the entire disclosure of which is herein incorporated by reference.

STATEMENT REGARDING FEDERALLY SPONSORED RESEARCH OR DEVELOPMENT

This invention was made with government support under Contract No. HR0011-12-1-0003, awarded by the Defense Advanced Research Projects Agency (DARPA). The government has certain rights in the invention.

FIELD OF THE TECHNOLOGY

The present invention relates generally to assembly.

SUMMARY

In exemplary implementations of this invention, hierarchical, nanometer-precise assembly is performed: A first structural unit is attached to a solid substrate in a first fluidic flow. A second structural unit is attached to the first structural unit in a second fluidic flow, a third structural unit is attached to the second structural unit in a third fluidic flow, and so on, until a target structure comprising the structural units is assembled. The first, second, third and so on fluidic flows are separate and occur in order in a temporal sequence. The assembled target structure is removed from the solid substrate.

In this structure, attachments between the structural units are formed by nucleobase pairing. The nucleobases may be natural (e.g., A-T, C-G) or unnatural (e.g., Z-P).

In exemplary implementations of this invention, the main body of each structural unit comprises a DNA origami "brick". However, this invention is agnostic as to the method of formation of the bricks themselves. The main body of each brick may be roughly rectangular cuboid in overall shape, and may include four attachment sites ("docking stations") at which the brick may be attached to another brick by nucleobase pairing.

Each docking station may comprise a set of three elongated nucleic acid strands (a "tri-linker") tethered at one end to the main body of the brick. Each tri-linker may be encoded with a sequence of base pairs that specify what that docking station is compatible with. For example, a docking station on the top front of a brick may only be able to dock with a docking station on the bottom back of another brick. The bricks may be divided into multiple families of brick, where bricks in the same family cannot dock with each other, and where bricks in a family may be limited regarding which other families of bricks they can dock with. During the temporal sequence of the assembly process, a specific permutation of nucleobase pairs for an attachment site may be used repeatedly, in separate fluidic flows which occur at different times, to form attachments. The coding on a tri-linker may be, but is not necessarily, unique in a local address space, at least for a single fluidic flow.

The three strands of a tri-linker may be of unequal length. This configuration (with different length linkers within each tri-linker) can limit the movement of the bricks between each other, and can cause bricks, when assembled, to be slanted in opposite directions periodically every other brick. The tri-linkers are positioned so as to minimize interaction between tri-linkers on the same face of a brick. Also, the tri-linkers on a face of a brick are preferably positioned so that they cannot extend beyond that face in a direction parallel to that face (to prevent formation of undesirable links when in the presence of other bricks).

As the bricks are assembled, they form a sequence which can, at joints between bricks, go straight, turn left at a 90 degree angle or turn right at a 90 degree angle. Such a scheme can produce any arbitrary 2D pattern, and when combined with vertical stacking of the bricks, can achieve arbitrary 3D patterns. Alternately, for example, assembly of at least a portion of the structure may be entirely in-plane, and may involve bricks with different geometries (e.g., pentagons) and sequences of brinks with turns of different degrees (e.g., 108 degrees). For example, tri-linkers protruding from the "side" of the main body of a brick all in the same plane may be used for in-plane assembly. Directionality of turns may be enforced by rotation of tri-linkers, custom geometry tri-linkers or custom chemical modification of tri-linkers.

A fluidic assembly system may include sensors for taking measurements to assess yield or other performance metrics of a fluidic assessment step. For example, microscopy imaging of fluorescence from FRET fluorophores may be used for this purpose. For example, by using three different fluorophore pairs, FRET imaging can detect whether an assembly step yielded a right turn, left turn, go straight or no connection.

The structural units may be assembled into larger modules, and the larger modules may in turn be assembled into the target structure.

The target structure may be attached to, or mechanically contain, payloads. For example, the payload may be a drug.

In exemplary implementations of this invention, the use of sequential fluidic flows dramatically reduces the number of unique base pair sequences needed for addressing, as compared to a "single-pot" synthesis method. Further, the use of a hierarchical, scalable synthesis strategy (e.g., folding a sequence of bricks only by 90 degree turns or by vertical brick stacking) facilitates automation of design and assembly. In exemplary implementations of this invention, both design of a target structure and assembly of bricks into the target structure can be automated and computer-controlled. Furthermore, processors may analyze sensor measurements for real time or near-real time assessment of performance of an assembly step or set of assembly steps.

The description of the present invention in the Summary and Abstract sections hereof is just a summary. It is intended only to give a general introduction to some illustrative implementations of this invention. It does not describe all of the details of this invention. This invention may be implemented in many other ways.

BRIEF DESCRIPTION OF THE DRAWINGS

FIG. 1A is a diagram of a "brick".

FIG. 2A shows a side view of the brick; FIG. 2B shows a top view of the brick.

FIGS. 3A and 3B are diagrams illustrating twist correction. FIG. 3A shows a brick before twist correction; FIG. 3B shows the brick after twist correction.

In FIG. 5A, an assembly sequence goes straight. In FIG. 5B, an assembly sequence turns right. In FIG. 5C, an assembly sequence turns left.

The above Figures show some illustrative implementations of this invention, or provide information that relates to those implementations. However, this invention may be implemented in many other ways. The above Figures do not show all of the details of this invention.

DETAILED DESCRIPTION

In exemplary implementations of this invention, a structure is assembled from a plurality of bricks.

As used herein, a "brick" is a structural unit. A brick may be of any shape or size. The main body of a brick may be of any material composition.

FIG. 1A is a diagram of the approximate overall shape of the main body of a brick, in a prototype of this invention. The main body 101 of the brick is a DNA origami structure, which comprises 42 DNA helices (e.g., helices 105, 107, 109), being 3 DNA helices thick and 14 DNA helices long. The DNA helices are connected to each other by "staples", which are shorter strands of synthetically produced DNA. Neither stapler nor linkers (which protrude from the main body of the brick) are shown in FIG. 1A. The 42 helices represent a single DNA circular backbone "stapled" into shape by short synthetic (single stranded) DNA molecules. (Technically DNA is a polymer as it is a series of nucleic acid molecules concatenated together.)

Figure 1B:
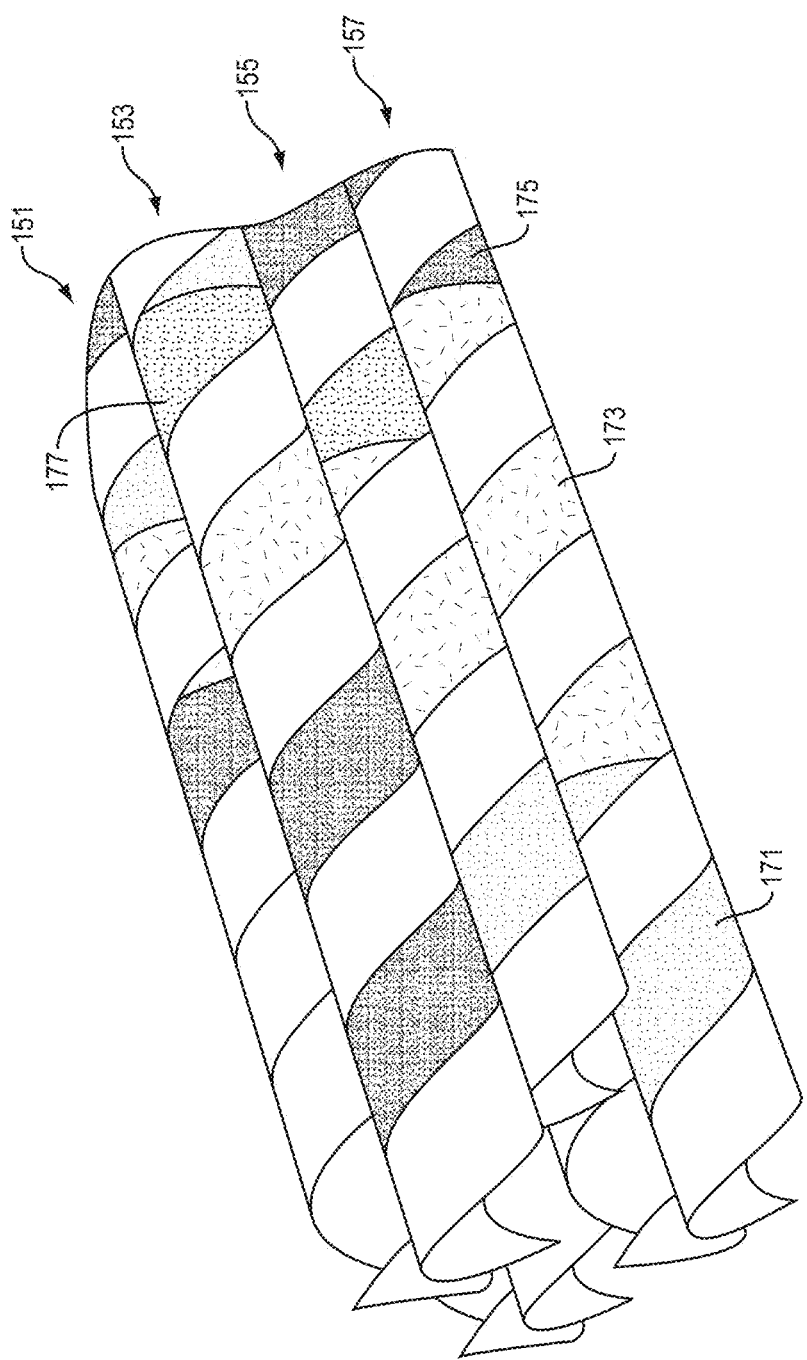
FIG. 1B is a diagram of a portion of a brick, showing staple attachment points.

FIG. 1B is a diagram of the approximate overall shape of a portion of the main body of brick, in this prototype. FIG. 1B shows 4 DNA helices 151, 153, 155, 157 in this portion, and shows areas in which DNA "staple" strands (e.g., 171, 173, 175, 177) connect to the DNA helices.

Figure 2A:
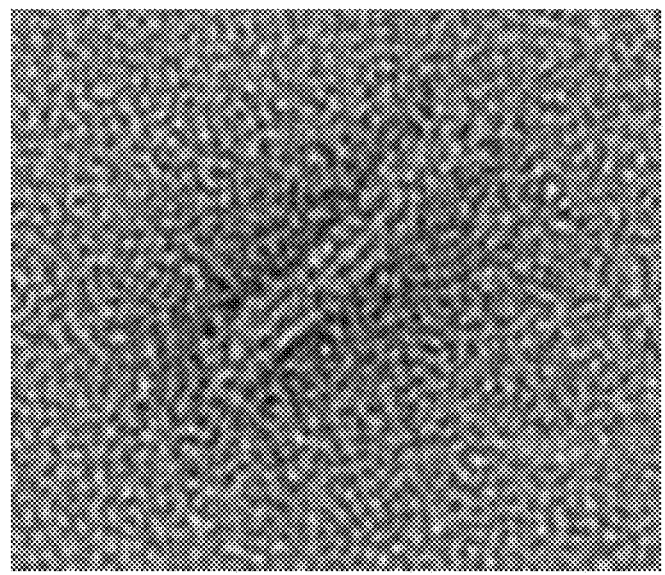
FIGS. 2A and 2B are transmission electron microscopy (TEM) images of a DNA brick.
Figure 2B:
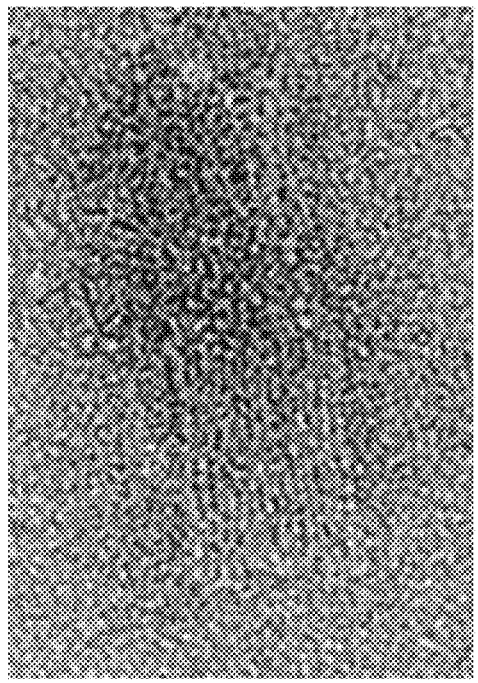

FIGS. 2A and 2B are transmission electron microscopy (TEM) images of the main body of a DNA brick, in a prototype of this invention. FIG. 2A shows a side view, in which three helices are visible. FIG. 2B shows a top view, in which fifteen helices are visible.

In this prototype, the main body of a brick has an overall 2/1 length/width ratio. This length/width ratio has at least two benefits: (a) it maximizes overlap between bricks when assembled; and (b) it facilitates debugging of assembly errors.

In this prototype, the main body of each brick, respectively, is created using a conventional DNA origami technique. This origami technique is described in Rothemund, P., "Folding DNA to create nanoscale shapes and patterns," Nature, Vol. 440, pp. 297-302, 2006. In this origami technique, single-stranded DNA (ssDNA) of the M13 bacteriophage is used, in conjunction with specifically-designed, synthetic DNA staple strands, to create 3D structures.

Specifically, in the prototype bricks shown in FIGS. 2A and 2B, M13mp18 phage DNA sequences are used for the ssDNA "backbones". The length of the staples is between 15 base pairs (bp) and 60 bp. This staple length helps facilitate optimal folding of the ssDNA in the bricks.

In this prototype, twist correction is performed on the overall structure of the main body of a brick. Twist correction is achieved by introducing skips in the design in precise quantity as to reduce the average base pair/helix turn metric to a desired value of 10.44. This allows overall approximate shape of the main body of the brick to be flat and not twisted.

FIGS. 3A and 3B are diagrams illustrating twist correction for a DNA brick. FIG. 3A shows the main body of a brick before twist correction; FIG. 3B shows the main body of the brick after twist correction. The angle between the longitudinal axes of helices 301 and 303 before twist correction (as shown in FIG. 3A), is greater than after twist correction (as shown in FIG. 3B).

In the prototype shown in FIGS. 1A, 1B, 2A, 2B, the bricks comprise DNA strands. However, this invention is not limited to DNA. For example, the bricks may comprise DNA, RNA, unnatural nucleic acids, and peptides. These materials can enable the attachment of different payloads and achieve geometries and functions that would otherwise not be possible. For example, the brick material can be changed to make the bricks less rigid thus allowing the bricks to buckle under specific loads or linking. Or, for example, the brick material can be modified to allow optimal binding of antibodies or other molecules to the structure therefore allowing biosensor applications.

In this prototype, the main body of a brick is roughly a rectangular cuboid in shape. However, other brick geometries may be used in this invention. The brick geometry is determined by, among other things, material composition, length and intrinsic material properties. The variation of brick geometry through the change of any of these characteristics allows greater flexibility in the resulting assembled structures. This helps achieve particular properties of the assembled structure and thus their applications. An example of this would be the use of pentagonal and hexagonal bricks to create spherical structures. Depending on the specific application one has in mind for the assembled structure, one may want to optimize the brick geometry to, for example, fill space, position precisely in space or isolate/group components precisely and in a controllable fashion.

In the prototype shown in FIGS. 1A, 1B, 2A, 2B, the bricks are produced using the conventional DNA origami technique described above. However, this invention is not limited to any particular method of making the bricks. For example, the bricks in this invention may be produced by: (1) a single-stranded tile (SST) technique, such as described in Wei, B., Dai, M., Yin, P., "Complex Shapes self-assembled from single-stranded DNA tiles", Nature, Vol. 485, May 31, 2012; (2) conventional DNA origami (with ssDNA strands and shorter DNA staples); (3) any other method of DNA folding or DNA nanoassembly, including methods using DNA tiles, DNA scaffolds, DNA lattices, four-armed junctions, double-crossover structures, nanotubes, static DNA structures, or dynamically changeable DNA structures, or (4) any other synthetic biology technique. Any approach that achieves the desired brick geometry, material composition and linkability may be employed. Furthermore, the bricks may include heteroelements, including proteins, metallic particles, quantum dots and fullerenes.

In exemplary implementations of this invention, bricks are linked together using 1 or 2 tri-linkers. Each tri-linker is a set of three single-stranded DNA molecules, where each of these three molecules, respectively, is tethered on one end to the main body of the same brick.

Figure 4:
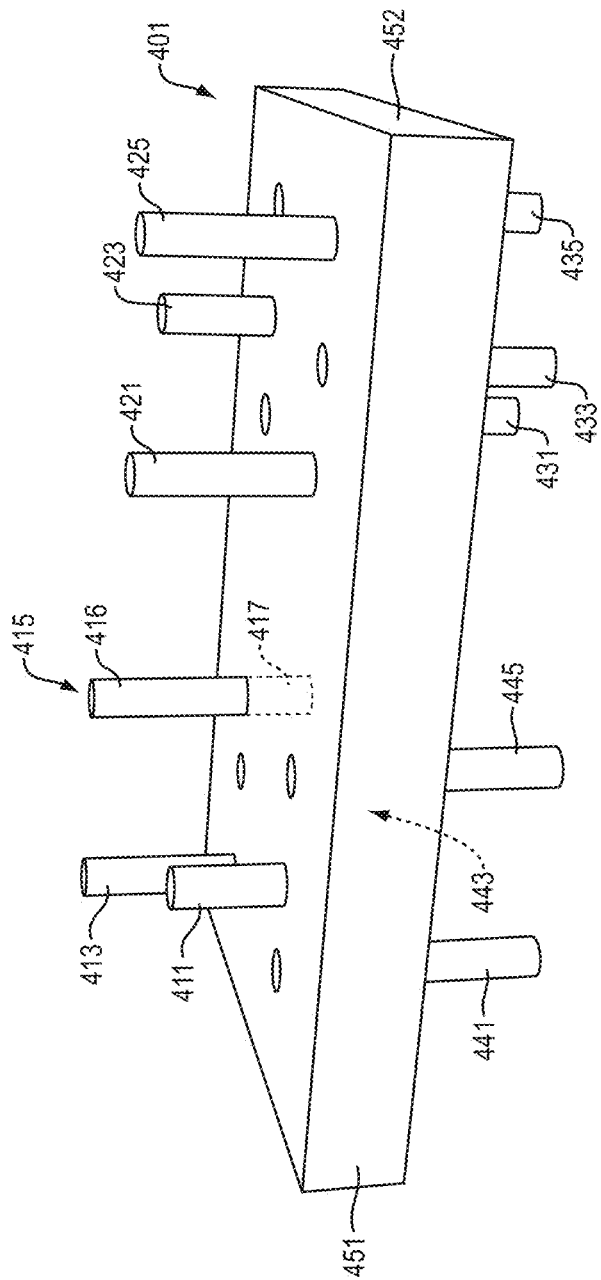
FIG. 4 is a diagram that shows linkers on a brick.

FIG. 4 is a diagram that shows four tri-linkers on a brick 401. In FIG. 4, DNA molecules 411, 413, 415 comprise a first tri-linker, DNA molecules 421, 423, 425 comprise a second tri-linker, DNA molecules 431, 433, 435 comprise a third tri-linker, and DNA molecules 441, 443 and 445 comprise a fourth tri-linker. (Molecule 443 is obscured from direct view in FIG. 4). Each of these DNA molecules, singly, is a "linker".

Each tri-linker encodes a docking position for a brick or functional group. In the example shown in FIG. 4, two linkers in a tri-linker are longer than the third linker in that tri-linker. This configuration (with different length linkers within each tri-linker) can limit the movement of the bricks between each other, and can cause bricks, when assembled, to be slanted in opposite directions periodically every other brick. Alternately, all 3 linkers in a tri-linker can be the same length.

In the example shown in FIG. 4, each tri-linker comprises three linkers arranged in a triangular configuration, where the distance between linkers is far enough to minimize or eliminate interaction between two or more of the linkers within the same tri-linker. In this example, there are 4 tri-linkers per brick, 2 on the top plane and 2 more on the bottom plane. The tri-linkers are arranged to be symmetric from each other with center of symmetry in the center of the face of the brick from which the linkers protrude. The tri-linkers are positioned in such a way that the reach of each linker does not extend outside the brick edges. In the example shown in FIG. 4, each of the four tri-linkers, respectively, functions as a docking position. The four positions are referred to as Front Top (FT), Front Bottom (FB), Back Top (BT) and Back Bottom (BB). The directionality of two bricks, when linked together by linkers, can be determined by the specific sequence of the DNA on the linkers, by rotation of the linkers, by custom geometry linkers or by chemical transformation of linkers. Alternatively, the main body of the bricks can include a physical code (e.g., DNA base pairs or codons) to identify them and determine orientation.

In the prototype shown in FIGS. 1A, 1B, 2B, 2C, each linker is a minimum of 15 base pairs (bp) long in order to achieve sufficient variability in the code of each linker, in order to improve the specificity of binding bricks to each other.

However, linker length can be varied in order, for example, to increase or decrease binding sequence space between bricks, increase or decrease distance between bricks or alter mechanical properties of the assembly. A linker is divided in two domains: a brick anchoring domain (e.g., domain 417 of linker 415 in FIG. 4) and a linker binding domain (e.g., domain 416 of linker 415). The length of these domains is constrained by the geometrical and mechanical constraints of the assembly. An aggregated length of 35 bp (15 anchor plus 20 linker binding) is used in this prototype as it allows a separation of ~6.6 nm between bricks of two different steps. However, the theoretical aggregate linker length minimum required for this invention is 2 bp and has no theoretical maximum length.

Linker sequence composition can vary based on the same geometrical and mechanical constraints as well as number of addressable linkers needed. Each linker binding domain (e.g., 416) may be, but is not necessarily, unique within a local address space, at least for a single fluidic flow. However, a linker binding domain is typically not unique in a global address space for an entire assembled structure, if the structure contains a large number of bricks (e.g., more than 100).

Consider the following example of when the linker domain may not be unique within a local address space: In some implementations of this invention, multiple sites are grown at once. If so, the following scenario can occur: multiple bricks have the same exposed sites and grow parallel branches by flowing one kind of brick only in a given fluidic flow.

Addressing can be implemented with nucleobase sequences. Also, addressing can be implemented by varying features of the sequence, including (a) the GC content (percentage of nucleobases in the sequence that are either guanine or cytosine) or (b) specific repeating motifs. Optimal length and sequence is highly dependent on the conditions used for assembly, themselves dependent on the final assembly goal. Thus, the length of linkers and the sequences used within linkers vary based on the application.

In the example shown in FIG. 4, one tri-linker (comprising three linkers) is used for each docking position. However, this invention is not limited to tri-linkers. Instead, the number of linkers used at each docking position can vary. Varying the number of linkers per docking position can affect the mechanical flexibility of the resulting assembly, and the specificity and direction of brick linking. In many applications, 3 linkers per docking site are sufficient. However, this invention can be implemented with one linker per docking site (a mono-linker), or two linkers (a bi-linker) at a docking site. Alternately, more than 3 linkers per docking position can be used—up to the number of linkers that as is physically allowed by the size and material composition of the brick.

This invention is not limited to the linker positions shown in FIG. 4. The position of one or more of the linkers on the brick can be varied. Indeed, any specific linker position can be used, as long as the linking allows differential orientation of the bricks. For example, the linkers could be placed on sides (e.g. sides 451, 452 in FIG. 4) of the bricks to achieve in-plane assemblies. Certain applications may require different angle values to be used for the assembly turns. Instead of 90 degree turns in the linker positioning to implement left and right turns, the linker positions can be altered to allow for different angle values in turns. For example, 108 degree turns can be used for the sequential assembly of a pentagon using 5 bricks. Or, for example, in-plane assemblies (using linkers on the edges of bricks) can be used to make deposition masks for electronics fabrication.

In exemplary implementations this invention, each linker comprises a DNA molecule. However, in other implementations of this invention, linkers can be made with other materials to achieve different properties. For example, DNA based linkers can be replaced with two-component protein systems that may exhibit stronger binding strength. Linkers binding could also be implemented chemically or mechanically.

In exemplary implementations of this invention, bricks are assembled into sequences of bricks ("assembly sequences"). Each assembly sequence is two or more bricks long. For example, an assembly sequence may be hundreds of bricks long, and may branch and link with other assembly sequences.

Figure 5A:
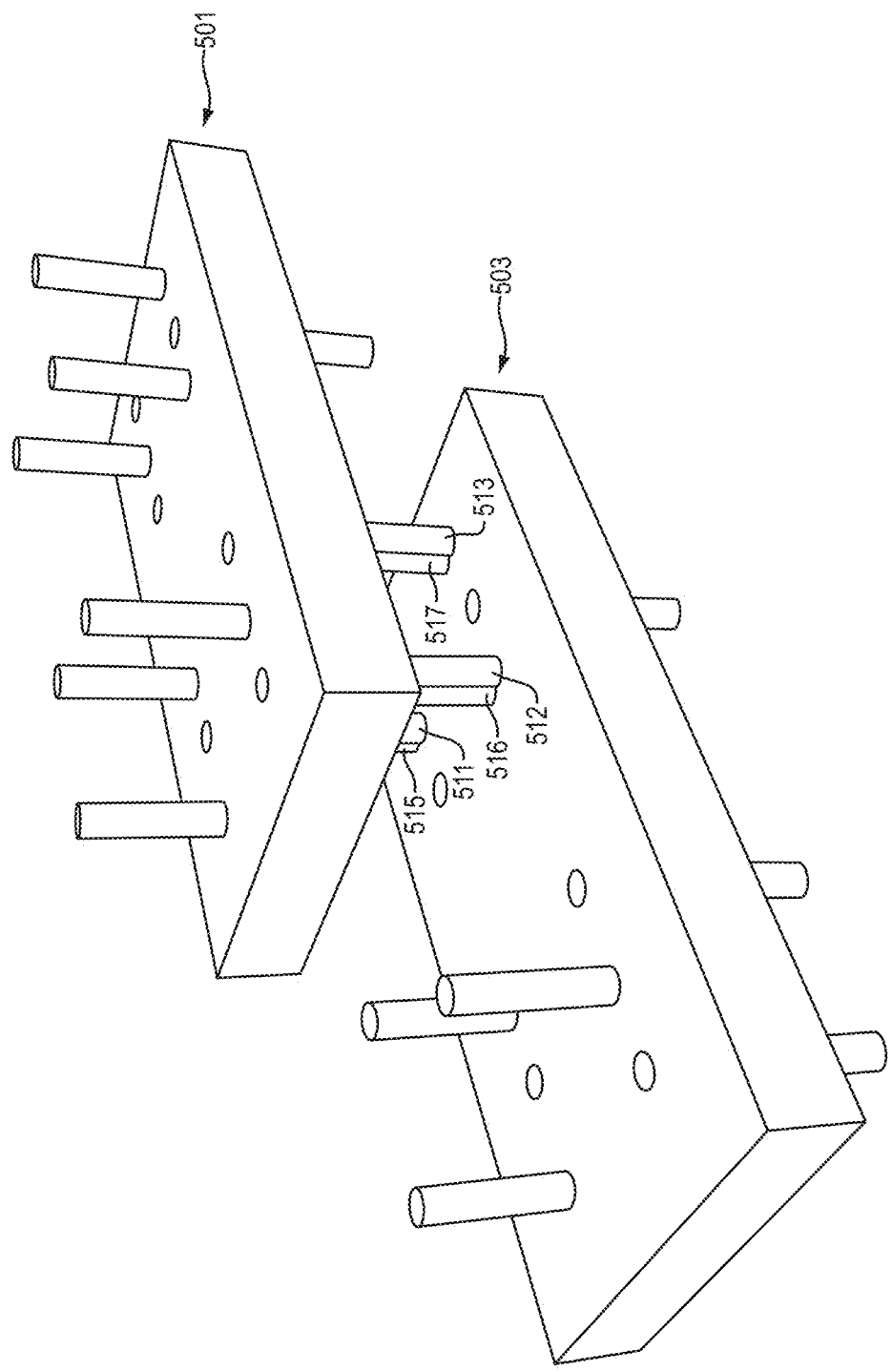
FIGS. 5A, 5B and 5C are diagrams that show sequences of bricks ("assembly sequences") that change direction at a 90 degree angle or go straight.
Figure 5B:
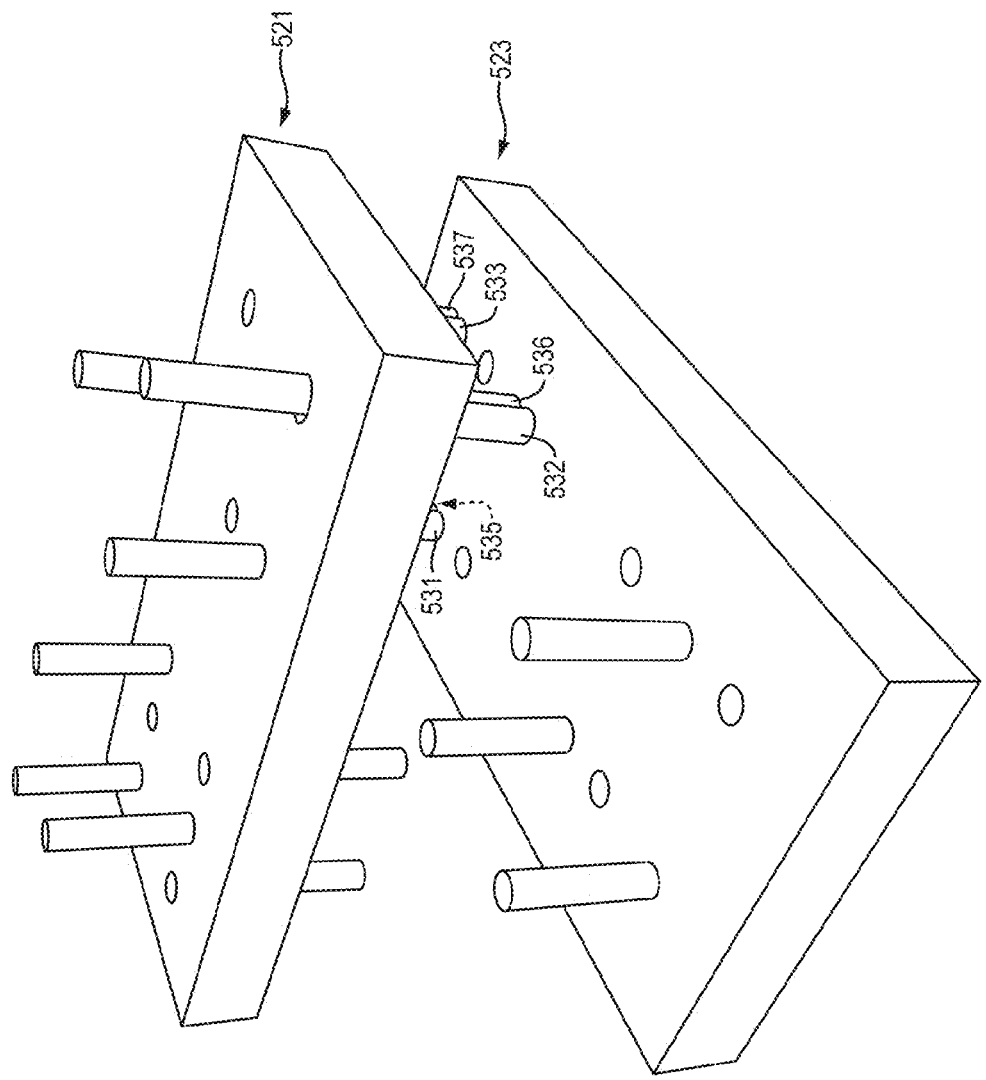
Figure 5C:
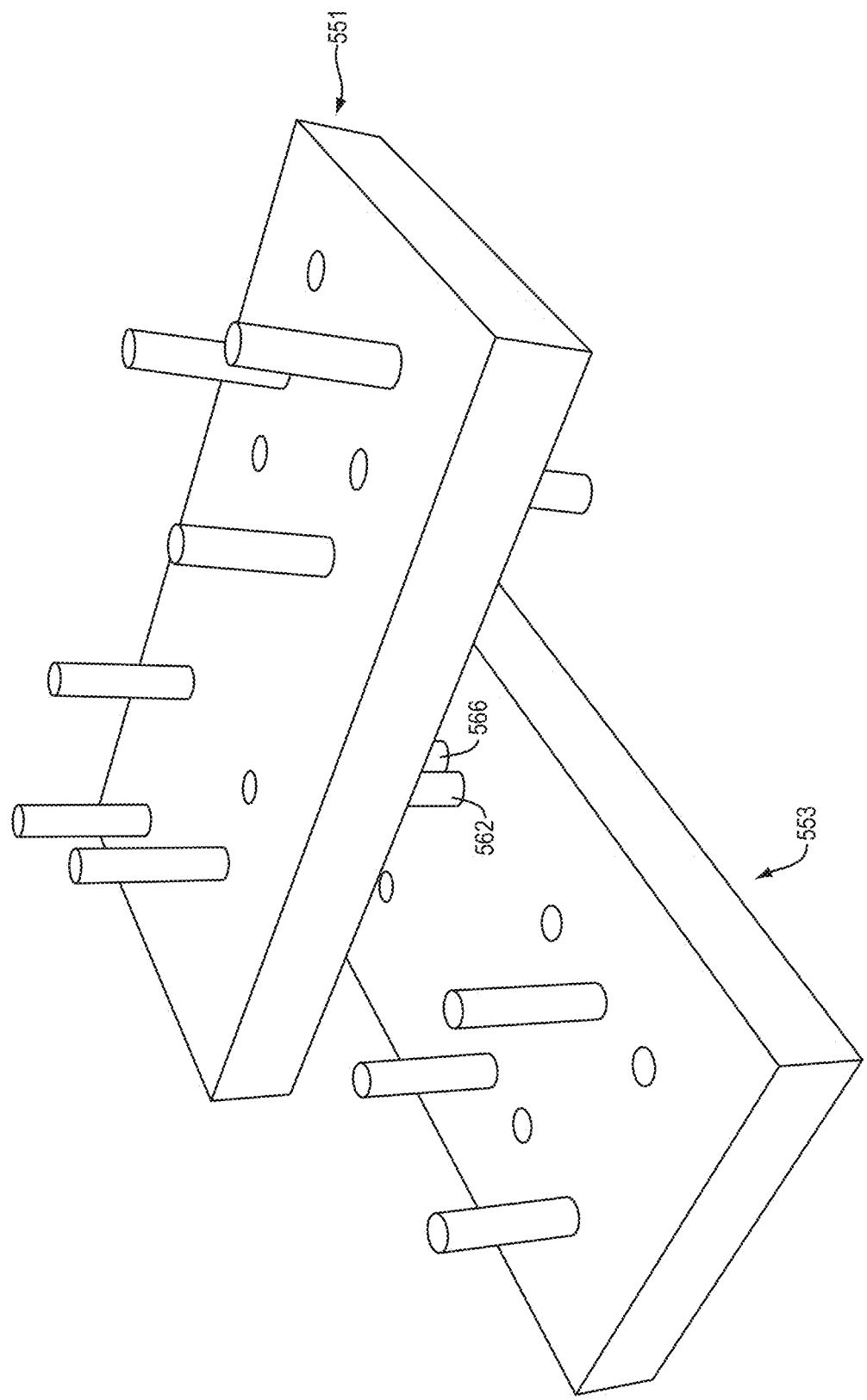

Each assembly sequence can change direction—that is, the direction of the sequence can vary spatially. FIGS. 5A, 5B and 5C show examples of sequences going straight, turning right by 90 degrees and turning left by 90 degrees. In each of these examples, a tri-linker tethered to one brick is attached to a tri-linker tethered to a second brick. The two tri-linkers are attached to each other by base pairing (e.g., by nucleobase pairing of cytosine/guanine and adenine/thymine). This attachment between the two tri-linkers forms a joint between the two bricks.

In FIG. 5A, an assembly sequence goes straight. The sequence comprises two bricks 501, 503. A first tri-linker in the top right docking position of brick 503 comprises linkers 511, 512, 513. A second tri-linker in the bottom left docking position of brick 501 comprises linkers 515, 516 517. These two tri-linkers are attached to each other by base pairing.

In FIG. 5B, an assembly sequence turns right at 90 degrees. The sequence comprises two bricks 521, 523. A first tri-linker in the top right docking position of brick 523 comprises linkers 531, 532, 533. A second tri-linker in the bottom left docking position (according to the notation used to describe FIG. 4) of brick 521 comprises linkers 535, 536 537. The two tri-linkers are attached to each other by base pairing.

In FIG. 5C, an assembly sequence turns left at 90 degrees. The sequence comprises two bricks 551, 553. A first tri-linker in the top right docking position of brick 553 includes linker 562. The second tri-linker in the bottom left docking position of brick 551 includes linker 566. The other linkers in these tri-linkers are obscured from view in FIG. 5C. The two tri-linkers are attached to each other by base pairing.

In exemplary implementations of this invention, joints configured to go straight, turn right by 90 degrees, and turn left by 90 degrees, can be used to assemble the bricks into any 3 dimensional (3D) shape. Going straight or making 90 degree turns allows an assembly sequence to achieve an arbitrary 2 dimensional shape. Stacking of bricks at joints can be used to achieve vertical height, in order to achieve a third dimension. For example: (a) in the joint shown in FIG. 5A, brick 501 is stacked on top of brick 503; (b) in the joint shown in FIG. 5B, brick 521 is stacked on top of brick 523; and (c) in the joint shown in FIG. 5C, brick 551 is stacked on top of brick 553.

Alternately, linkers positioned on the sides of bricks (e.g., sides 451, 452) can attach to linkers on the top or bottom of bricks, in order to facilitate the assembly of full 3D structures. This alternative implementation can reduce the number of bricks required to go in the third dimension.

Or, alternately, linkers from the sides of the bricks can attach to other linkers, also on the side of the bricks to achieve a planar (2D) growth as the bricks wouldn't stack anymore and just link side by side.

In exemplary implementations of this invention, coded folding of assembly sequences is employed. The coding may employ local addressing rather than global addressing. For example, a code on a linker may be a local address that specifies the type(s) of docking positions with which the linker is compatible, or family(ies) of bricks with which the linker is compatible.

It is known that an arbitrary three-dimensional structure may be created by folding a one-dimensional string. Such folding can be implemented with as little as 1 bit of state at each joint, corresponding to left or right folds in right-angle tetrahedra or hexagonally-bisected cubes. See Cheung, K., Demaine, E., Bachrach, J., Griffith, S., "Programmable Assembly With Universally Foldable Strings (Moteins)", IEEE Transactions on Robotics (27:4), pp. 718-729 (2011).

In some implementations of this invention, complex structures are hierarchically assembled from modules (e.g., tileable cubes with unique face pairings). Each of these modules may comprise multiple bricks. The use of modules simplifies path planning, and speeds up assembly. Functional payloads can be contained within modules, or linked between them.

In exemplary implementations of this invention, bricks are joined by base pair bonding. The base pairing may involve naturally occurring base pairs (e.g., cytosine/guanine, adenine/thymine or adenine/uracil) or unnatural base pairs (e.g. Z-P base pairs), or base pairs that include at least one unnatural nucleobase. Alternately, any other physical code may be employed (e.g., code involving complementary proteins and ligands, or code involving ligands and other molecules).

Effectively, linkers (or sets of linkers, such as tri-linkers) have a physical code that allows them to attach to other linker (or sets of linker, such as tri-linkers). Alternatively, there might be an intermediary bridge linker that may mediate the linking of two bricks. The reason for such a bridge linker would be to have some selective code for removing it using strand displacement or other mechanism to enable reconfiguration of the geometry after it was built.

In order to enforce direction, linkers may be rotated on the bricks. This rotation can be done on either brick (fixed brick or incoming brick).

In some implementations of this invention, one or more of the bricks in an assembly sequence are pre-neutered bricks. As used herein, a "pre-neutered brick" means a brick that has no protected tri-linkers (and the no protected linkers), they are all exposed. In many cases, a pre-neutered brick has only 2 attachment sites: one to attach to the growing structure and a second to allow new bricks to attach to it. In other cases, a pre-neutered brick has three or more attachment sites. An advantage of using pre-neutered bricks is that it may avoid the need for activation of docking positions on bricks during assembly of bricks (e.g., activating a site on a first brick, before flowing a second brick to attach to it). A disadvantage of using pre-neutered bricks is that it increases the number of bricks required to allow assembly of every permutation of geometries.

Figure 6:
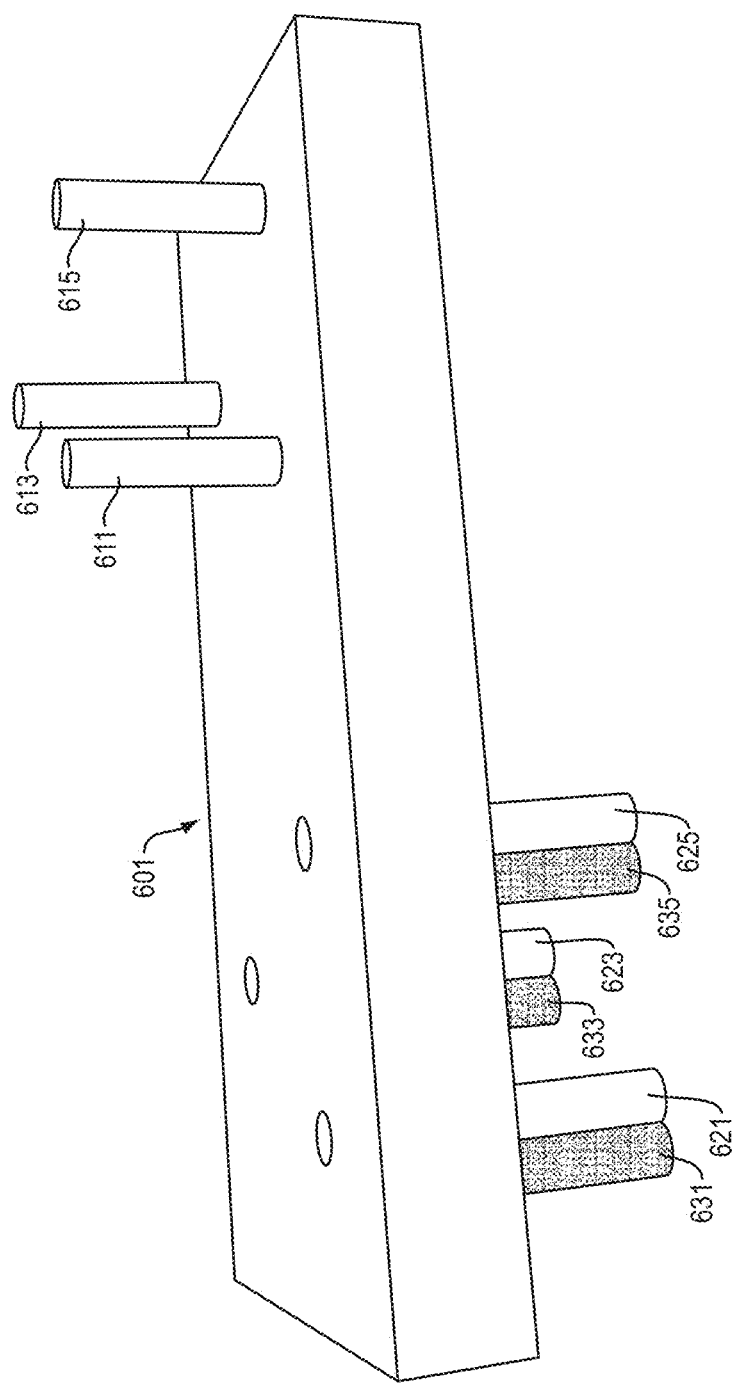
FIG. 6 is a diagram of a "pre-neutered" brick.

FIG. 6 is a diagram of a "pre-neutered" brick. In the example shown in FIG. 6, a pre-neutered brick has two tri-linkers: a first tri-linker tethered to the bottom of brick and a second tri-linker tethered to the top of the brick. The first tri-linker comprises linkers 621, 623, 625; the second tri-linker comprises linkers 611, 613, 615. In the example shown in FIG. 6: (a) the second tri-linker is not yet attached to any other brick; and (b) the first tri-linker is attached to tri-linker of another brick (comprising linkers 631, 633, 635).

In exemplary implementations of this invention, a system precisely assembles bricks into a desired structure (target structure). The system uses microfluidic techniques to flow precise quantities of different bricks and other materials in a timely fashion into a growth chamber where the target structures are built. For example, the other materials may comprise oligonucleotides, proteins, inorganic compounds and living organisms. Microfluidic devices in the system can selectively collect or discard the flow-throughs.

One or more processors control the system. For example, the one or more processors can (a) control actuation of microfluidic components; (b) process data relating to the assembly of the structures; (c) make decisions based on feedback; and (d) control the system to optimize conditions for the correct assembly of the target structures.

The system includes one or more growth chambers. Each growth chamber is a microfluidics device where the assembly of a target structure may occur. For example, each growth chamber may comprise a glass-based flow cell, PDMS microfluidics, or an electrowetting digital fluidic chip. For example, growth chambers may perform solid phase synthesis in a column, multi-well or array on flat surface format.

This invention is not limited to flat growth chambers. Assembly sequences can be grown on beads in a column, on the sides of a column, in a multiwell plate or on a flat surface where we have multiple growing sites arrayed along the surface.

Fluidic components of the system: (a) can move, or allow movement of, materials from their storage medium to the growth chamber; (b) can selectively collect and discard excess material and flow through; and (c) can be controlled electronically. In some but not all implementations, the fluidic components use constant pressure supplies and controllable pinch valves. Alternately, other liquid handling techniques can be employed, including digital liquid handling platforms.

The system can automate assembly of a target object. Software may be encoded in tangible, machine-readable media (e.g., one or more electronic memory devices in the system).

This software includes instructions for one or more computer processors: (a) to decompose an object design into left, right and straight turns; (b) translate those turns into microfluidic instructions for the valves and actuation devices; (c) process data indicative of measurements by sensors (e.g. measurements by optical sensors of signals emitted by FRET pairs), in order to assess assembly yield, at different steps of the assembly process; (d) store the step yield value at each step of the design; (e) perform machine learning, based at least in part on these stored yield value, to increase efficiency of subsequent assemblies; and (f) if the system is using a dynamic linking strategy (e.g., linkers with oligo toeholds), output instructions to undo specific steps of the assembly. This software includes algorithms for actuation of hardware and for sensing/feedback loops.

The system includes one or more sensors for assessing assembly yield at different steps in a sequential assembly process (wherein bricks are assembled into a target structure). The sensors take measurements which are used as feedback in the assembly process and used to facilitate debugging of the assembly process. One or more computer processors analyze signals indicative of the sensor measurements, in order to assess metrics regarding the assembly process (including to assess parameters indicative of the extent to which a previous step of a sequential assembly process achieved a specified result). For example, the sensors may comprise (a) fluorescent microscopy imaging devices, (b) other optical sensors, (c) capacitive sensors, or (d) impedance sensors, voltmeters, or ammeters.

For example, fluorescent imaging of FRET (Forster resonance energy transfer) pairs may be employed in order to assess yield of each assembly step. FRET fluorophores may be attached to anchor sites on the bricks. A fluorescent microscopy imaging device may take images that measure fluorescent intensity (e.g., of donor fluorophores). One or more processors may analyze these images for differential detection of four different states: no brick attachment, left turn attachment, right turn attachment and straight attachment.

This invention can be implemented by using alternate feedback technology. For example, high frequency relaxation can be employed to assess the assembly state of two bricks.

In a prototype of this invention, FRET-based sensing uses 3 different fluorophore pairs. An alternative implementation would be to increase the number of distinct fluorophore pairs to obtain more information about the assembly state of the structure. (The number of distinct fluorophore pairs can be increased to as much as is allowed by space constraints and crosstalk between fluorophores). Alternately, a feedback mechanism using a little as two distinct fluorophore pairs can be implemented, albeit with reduced knowledge of the assembled state.

Without being limited by theory: FRET works by inputting energy (usually light) into a donor half of the pair, which when in close enough proximity to the acceptor half of the pair it transfers its energy to it. The acceptor usually dumps that energy by emitting light. The pair is chosen such that if they are not in close proximity the donor molecule emits light at a different wavelength than the acceptor would. Hence you're able to tell if something is close to something else at very small distances (relationship scales with $6^{th}$ power). In this prototype, what is likely to occur is that the donor part of the fluorophore pair will be positioned in such a way as to be shared by the three acceptors. However, only based on the geometry and orientation of the bricks relative to each other will the two sides (donor and acceptor) come into enough proximity for FRET interaction. That's why there are 3 distinct pairs in this prototype. Alternately, three distinct fluorophore pairs with all 6 parts (3 donors and 3 acceptors) are used—which is still 3 pairs.

Different sensor assessment technologies influence the growth chamber topology and composition. For example, even in a single implementation of this invention, the system may have multiple growth chambers, each of which, respectively, uses different sensing modes.

Figure 7:
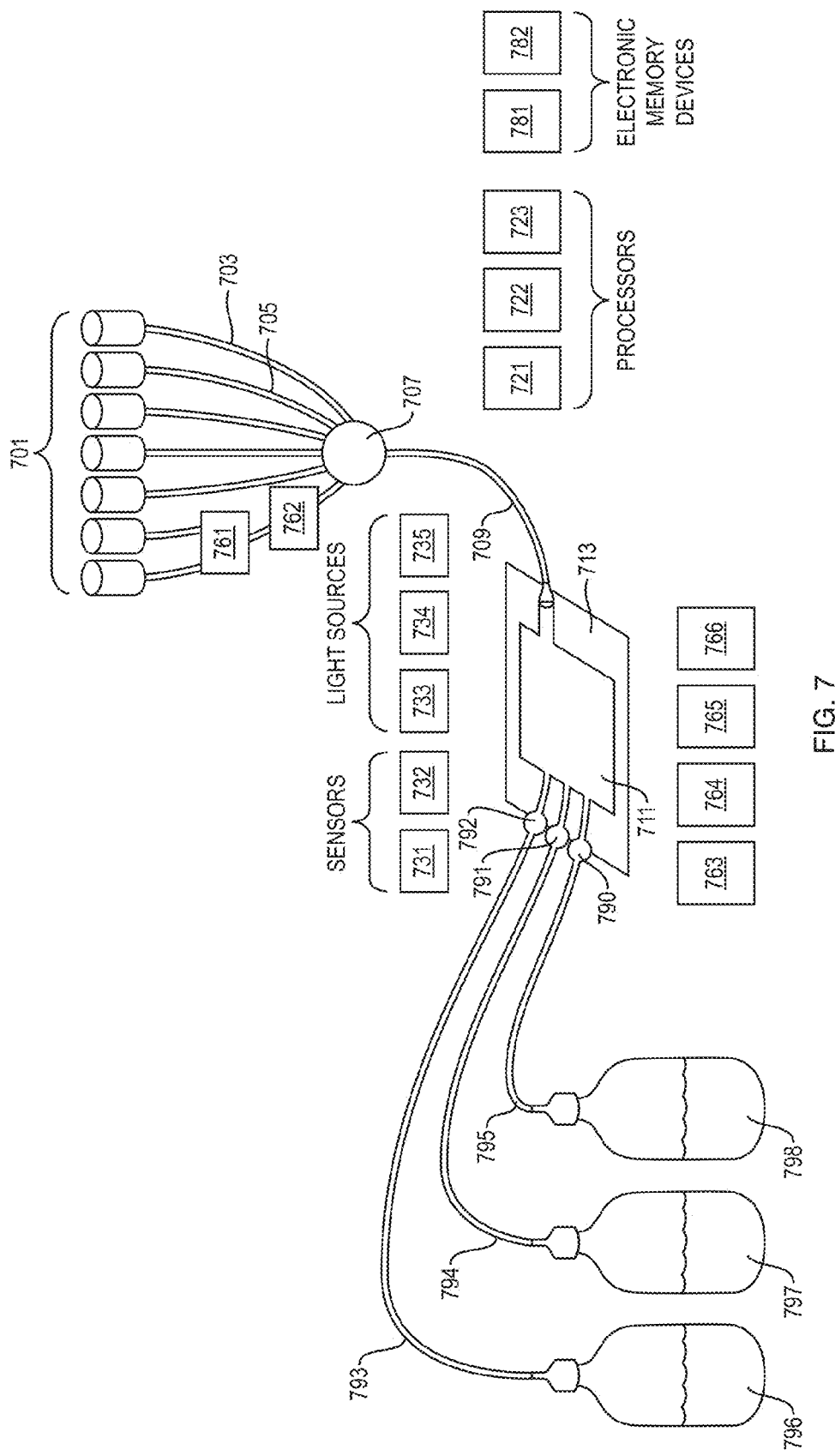
FIG. 7 is a diagram of a system for assembling bricks into a structure.

FIG. 7 is a diagram of a computer-controllable system for fluidic assembly of bricks into a target structure, in a prototype of this invention. A plurality of containers 701 holds materials used in the assembly process. For example, each container may hold a different material. For example, the materials may comprise one or more types of bricks, buffers, catalysts, enzymes, nucleotide residues, materials used in oligonucleotide synthesis, materials used in toehold-mediated strand displacement, proteins, metallic particles, quantum dots, fullerenes, streptavidin, biotin and payloads for the target structure. Tubing (e.g., tubes 703, 705) is employed to transport the materials from the containers 701 to a multiple-input computer-controllable valve 707. The valve 707 controls which materials are transported via tubing 709 from the valve 707 to a growth chamber 711. In the growth chamber 711, the target structure is grown in sequential steps. Multiple outlets from the growth chamber 711 allow output to be harvested or trashed after various assembly steps. For example, multiple valves (e.g. valves 790, 791, 792) can control whether output is removed through an output tube (e.g., 793, 794, 795) to an output collection bottle (e.g., 796, 797, 798).

One or more sensors (e.g., 731, 732) and a disposable flow/imaging cell 713 are used for taking sensor measurements to assess yield and other parameters of different assembly steps. One or more light sources (e.g., 733, 734, 735) may be employed. For example, if FRET imaging is used, a light source may shine light at a frequency that will excite the donor fluorophore of one pair but not substantially excite other donor fluorophores. The fluidics devices may be microfluidic devices.

Optionally, a pump or other actuator 761 may be used to actuate fluid movement, and a mixing chamber 762 may be used to mix or dissolve materials. Optionally, heaters 763, coolers 764 or heat exchangers 765 may be used to raise or lower temperatures in order to facilitate desired reactions. More generally, any one or more Known components (e.g., 766) of a fluidic system (including a microfluidic system) may be employed in this invention.

This invention is not limited to the particular example of an assembly system shown in FIG. 7. The number and position of the items shown in FIG. 7 may vary. More generally, the hardware, software, functionality, size, geometry, and material properties of the assembly system may vary, depending on the particular implementation of this invention. For example, the substrate material used in a growth chamber may vary, depending on particular implementation. The substrate material may permit anchoring of an initial "seed" linker either through chemical modification or preparation of the material. For example, glass or PDMS (polydimethylsiloxane) may be used for DNA anchoring. Or, for example, if parallel assembly sites are employed, specific assembly site wells may be etched into the bottom of the growth chamber, in order to reduce cross-talk between the parallel sites.

In exemplary implementations of this invention, different families of bricks are used. Tri-linkers of one family are physically coded (e.g., with nucleobases) so that they cannot bind to each-other as that would cause self-aggregation when flowed into a growth chamber. Instead, a tri-linker of one brick family can bind only to a tri-linker of another brick family. For example, consider two brick families: family 1 and family 2. These two brick families have the same main body, but the physical code of their respective tri-linkers is such that the front docking positions of family 1 bricks are compatible with the back tri-linkers of family 2 bricks. Use of multiple families of bricks facilitates efficient assembly of bricks into larger structures.

Figure 8:
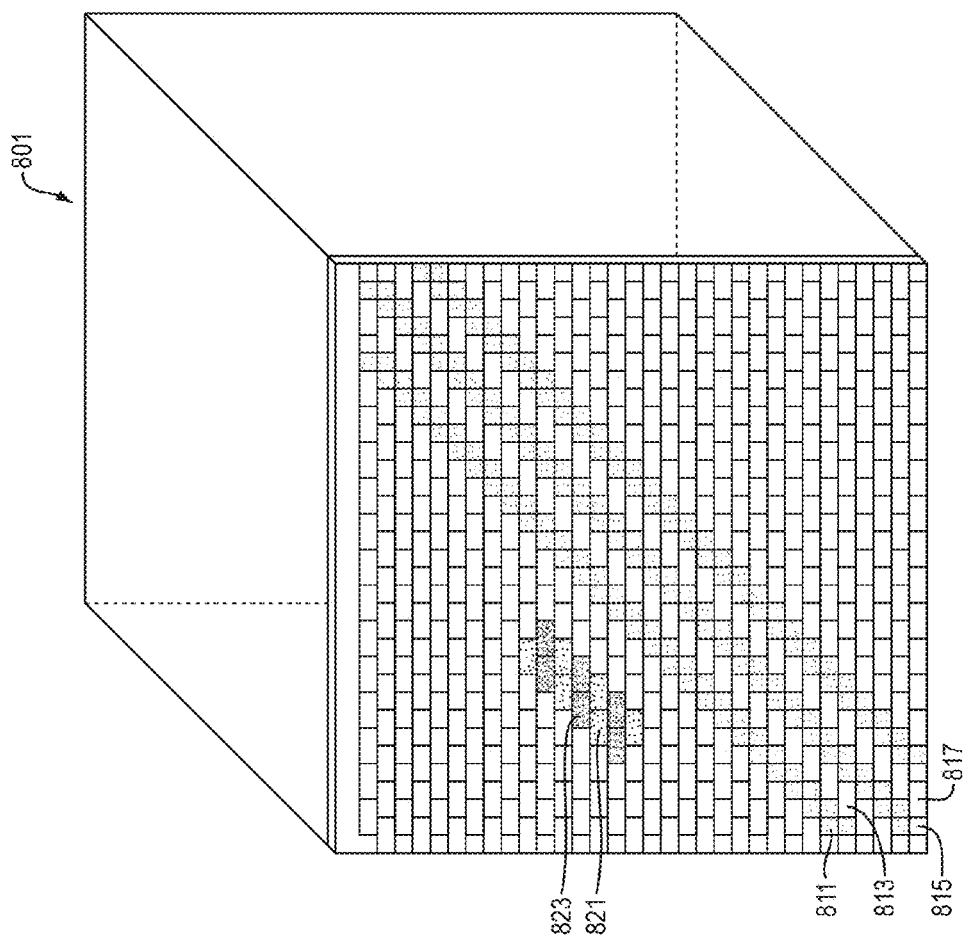
FIG. 8 is a diagram that shows use of different brick families in a wall of a structure.

FIG. 8 is a diagram that shows an example of different brick families used in a wall of a structure. In this example, a wall of a small structure 801 comprises a spatially periodic pattern with alternating families of bricks. In a portion of the wall, bricks in a first family (e.g., 821) alternate with bricks in a second family (e.g., 823). In another portion of the wall, bricks in a third family (e.g., 811, 815) may alternate with bricks in a fourth family (e.g., 813, 817).

Figure 9:
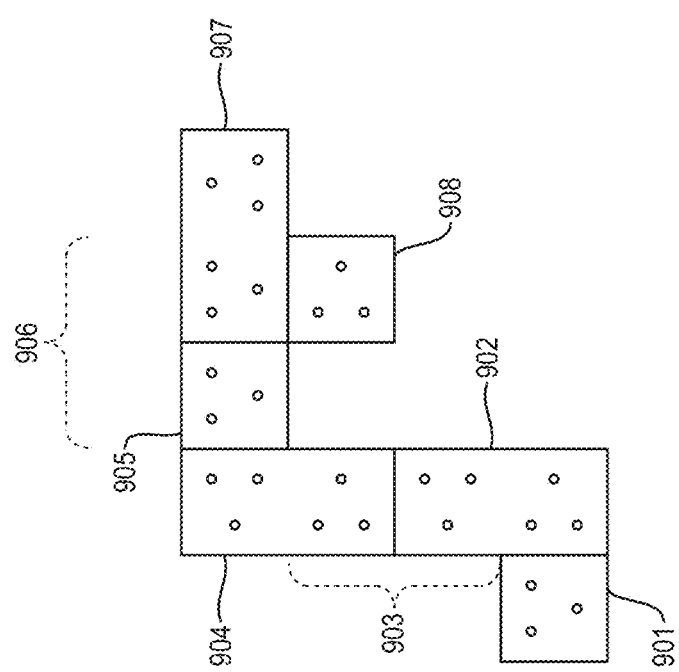
FIG. 9 is a diagram of a sequence of bricks.

FIG. 9 is a diagram of an example of a sequence of bricks which changes direction. The diagram shows an orthogonal top view of the sequence. In the following description of FIG. 9, "right" and "left" are from the perspective of a viewer traveling (face forward in the plane of the diagram) along the sequence from brick 901 to brick 907. In FIG. 9, brick 901 is a seed brick. The joint between bricks 901 and 902 forms a 90 degree left turn. Brick 902 is on top of part of brick 901. Part of brick 903 is underneath part of brick 902 and part of brick 903 is underneath brick 904; thus, brick 903 is not visible in FIG. 9. The joint between bricks 902 and 903 goes straight; and the joint between bricks 903 and 904 goes straight. The joint between bricks 904 and 905 forms a 90 degree right turn. Brick 904 is on top of part of brick 905. Part of brick 906 is underneath brick 905 and part of brick 906 is underneath brick 907; thus, brick 906 is not visible in FIG. 9. The joint between bricks 905 and 906 goes straight; and the joint between bricks 906 and 907 goes straight. The joint between bricks 906 and 908 forms a 90 degree right turn. A portion of brick 906 is (a) on top of brick 908 and (b) beneath brick 907. At the point where 906, 907 and 908 overlap, there is a 3 layer thickness.

Figure 10:
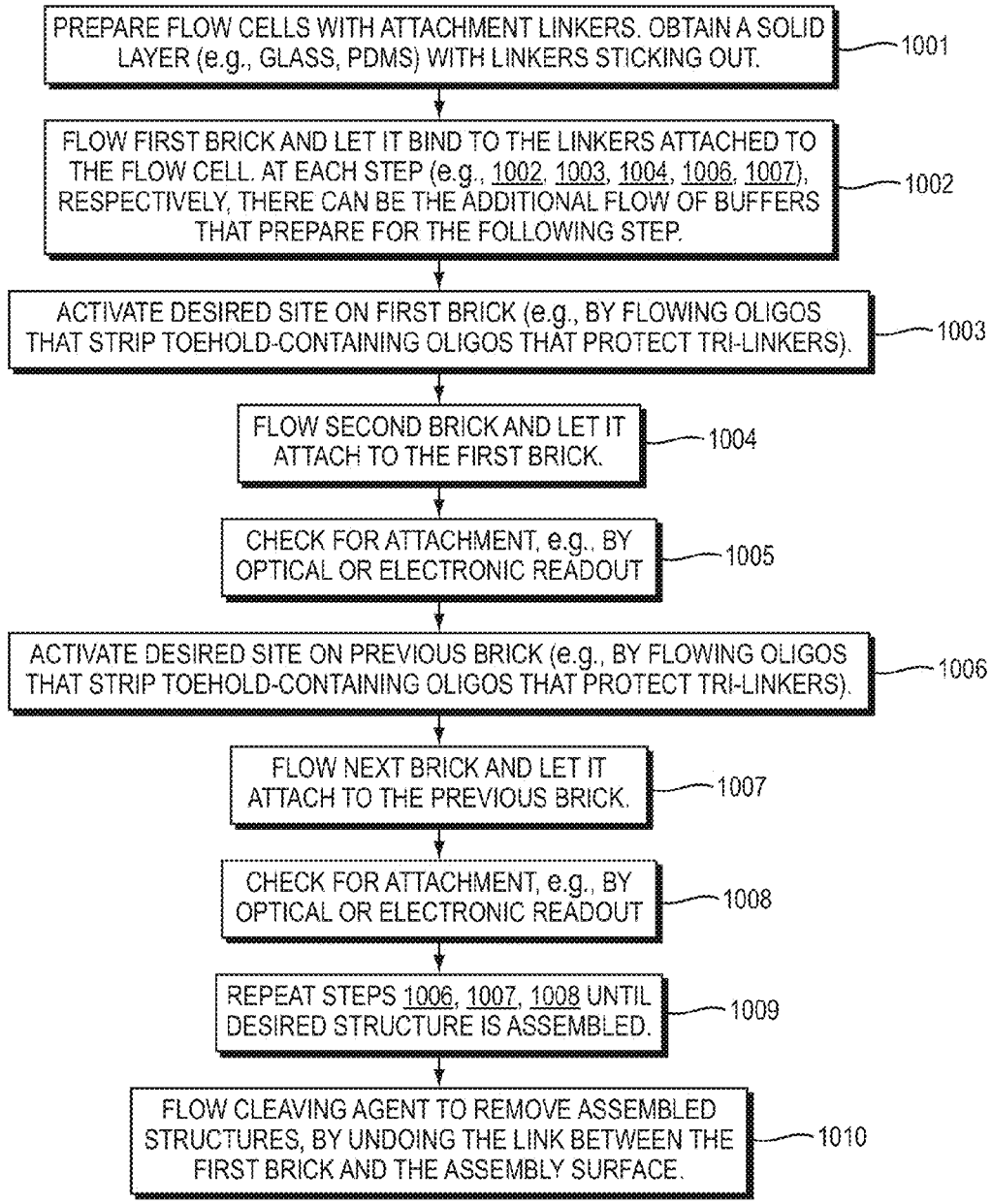
FIG. 10 is a flow chart of steps for assembling a structure using bricks.

FIG. 10 is a flow chart of steps for assembling a structure using brick, in exemplary implementations of this invention. In the example shown in FIG. 10, the steps are:

A. Prepare flow cells with attachment linkers. Obtain a solid layer (e.g., glass, PDMS) with linkers sticking out 1001.

B. Flow first brick and let it bind to the linkers attached to the flow cell.

At each step (e.g., steps B, C, D, F, G), respectively, there can be the additional flow of buffers that prepare for the following step 1002.

C. Activate desired site on first brick (e.g., by flowing oligonucleotides that strip toehold-containing oligonucleotides that protect tri-linkers) 1003.

D. Flow second brick and let it attach to the first brick 1004.

E. Check for attachment, e.g. by optical or electronic readout 1005.

F. Activate desired site on previous brick (e.g., by flowing oligonucleotides that strip toehold-containing oligonucleotides that protect tri-linkers) 1006.

G. Flow next brick and let it attach to the previous brick 1007.

H. Check for attachment, e.g., by optical or electronic readout 1008.

I. Repeat steps F, G, H until target structure is assembled 1009.

J. Flow cleaving agent to remove assembled structures, by undoing the link between the first brick and the assembly surface 1010.

For example, in steps E and H, optical readout may be by FRET imaging. If FRET imaging is employed, the color imaged in a microscope may be compared with colors expected given particular brick assembly combinations. The comparison may be performed automatically by sensors and one or more processors, or may be performed by a human being looking into a microscope.

In some implementations, if pre-neutered bricks are used, site activation (steps C and F) may be omitted.

In the assembly process, a linker may be protected or deprotected, in order to deactivate or activate a docking station on a brick. For example, simple hybridization may be employed to shield a linker from interacting. In simple hybridization, oligonucleotides complementary to the linker to be shielded are flowed into a growth chamber. Or, for example, nucleic acid strand displacement (including toehold-mediated activation) may be employed to deprotect a linker, thereby enabling the linker to interact. In strand displacement, one nucleic acid strand displaces a second nucleic acid strand, by binding to a third nucleic acid strand. Toehold mediated activation can be implemented, for example, by using a first oligonucleotide which contains a short hairpin sequence pattern in conjunction with a second oligonucleotide (a short unpaired "toehold" sequence), which toehold can be later removed by flowing in a third oligonucleotide. This allows a dynamic activation and termination of attachment sites, thus reducing the number of bricks necessary as building material. Furthermore, this toehold mechanism can also be applied to the linkers themselves to achieve dynamic linking between bricks and allow selective removal of misassembled bricks.

This invention is not limited to the particular assembly steps shown in FIG. 10. For example, other systems and methods may be employed to sequentially attach bricks in an assembly sequence, using physical codes on the respective bricks to ensure correct docking between bricks to form the desired geometry of the assembly sequence. For example, any Known compound, Known device and Known method used in any step of any technique of synthetic biology, RNA synthesis or DNA synthesis (including solid phase synthesis, oligonucleotide synthesis, and toehold mediated strand displacement) may be employed in assembling bricks into an assembly sequence. Also, for example, attachment at docking stations may be chemical, enzymatic or mechanical.

This invention is not restricted to a particular size of (i) target structure, (ii) main body of brick, or (iii) fluidic channels. For example, this invention can be implemented by moving smaller (e.g., nL) or larger (e.g., mL) amounts of bricks and buffers.

Nor is this invention restricted to a particular type or concentration of buffer. Depending on the particular implementation, buffers may be optimized by, among other things, varying salt concentration, mono and di-valent ions concentrations and large molecule concentrations (i.e.: PEG for molecular crowding assisted assembly).

Other possible variations include: Site activation can be omitted in some steps during assembly of an assembly sequence when using pre-neutered bricks as such bricks have no protected sites. Site activation steps may also be carried out chemically or enzymatically and not only via DNA toehold-removal. When attaching the next brick onto the previous one, additional steps may be taken to ensure a better link. This may include but is not limited to, temperature change, salt and ion concentration variation, chemical reactions and other mechanical steps like sonication or vortexing.

Solid phase synthesis may be employed for assembly of the bricks into assembly sequences (and for formation of the bricks themselves). However, this invention is not limited to solid phase synthesis. For example, in some implementations, assembly sequences may be assembled in solution without attachment to a solid substrate. Alternately, click chemistry may be employed to control folding of assembly sequences (or folding within bricks themselves).

In exemplary implementations of this invention, a target structure (formed by assembling bricks together) may carry a payload. Any conventional method of linking a payload to a structure may be employed, including: chemical bonding (e.g. DSSP), peptide tags (e.g., biotin-de-novo phage-display derived "selective velcro"), and mechanical coupling (e.g. nanoparticle in a cage).

In exemplary implementations of this invention, a target structure may carry any of a wide variety of payloads, including bio-nano organic and inorganic materials. Payload examples include: peptides, antibodies, bispecifics, nanoclusters, nanowires, nanoparticles, quantum dots, fluorescent dyes, and receptors.

This invention has many practical applications. For example, depending on the particular implementation:

(a) this invention may be used assemble 2D or 3D structures in the sub-100 nm range, including resonators, nanomagnetics (offering magnetic response at optical frequencies), strong electric dipole biocompatible nanoantennae, negative index of refraction structures, nano/bioplasmonics, bio-nano-photovoltaics/thermoelectrics, molecular logic gates, bio(qu)bits, and molecular sensor elements (designer receptors/transducers);

(b) this invention may be used to assemble 2D or 3D structures in the 100 nm-1 micrometer range, including molecular "QR codes", (~$10^3$ elements) for tagging materials and objects, and structures for cryptography, tracking and authentication;

(c) this invention may be used to assemble structures with more than 100,000 structural units, including 3D diffractive and holographic optical elements, micro lenses, gratings, surface acoustic wave device, molecular probes for spectroscopies (e.g., dielectric, impedance, inelastic electron tunneling, IR spectroscopy); and (d) this invention may be used to assemble biocompatible nm-precise micron-sized structures, including structures with 3D addressability for precise tethering of proteins, and structures used for single-cell measurements, biocompatible electrode attachment for photo-electronics, optoacoustic probes and synthetic biology interfaces.

In exemplary implementations of this invention, one or more tangible machine-readable media have instructions encoded thereon for causing one or more computer processors to perform one or more of the following functions (the "Processor Functions"): (1) to control the operation of hardware components of an assembly system, include valves, pumps, sensors, and light sources; (2) to control the assembly of bricks into assembly sequences and target structures; (3) to control the formation of bricks themselves; (4) to control sensors for assessing performance and yield of assembly steps; (5) to receive signals indicative of human input; (6) to output signals for controlling transducers for outputting information in human perceivable format, and (5) to process data, perform computations, and control the read/write of data to and from memory devices. In exemplary implementations, the one or more processors are specially adapted, by virtue of these instructions, to perform the Processor Functions. The one or more processors may be located in any position or position within or outside of the assembly system. For example: (1) some of the one or more processors may be embedded within or housed together with or adjacent to other components of the system, such as valves or a growth chamber; and (2) some of the one or more processors may be remote from other components of the device. The one or more processors may be connected to each other or to other components in the assembly system either: (1) wirelessly, (2) by wired connection, or (3) by a combination of wired and wireless connections. For example, rectangles 721, 722, 723 in FIG. 7 each, respectively, represent one or more of these computer processors. One or more electronic memory devices (e.g., 781, 782) may encode software instructions for the one or more processors in non-transitory, tangible form.

In some implementations of this invention, right-angle folds in assembly sequences can be implemented by using joints that bond only to links, and links that bond only to joints. These can be sequentially flooded and washed in a solid-phase synthesis, analogous to synthetic production of DNA. In these implementations, instead of reservoirs of adenine, guanine, cytosine and thymine, there are reservoirs of joints that enforce local fold directions, and linkers that can optionally be functionalized with nanocluster payloads to place inorganic materials.

In exemplary implementations of this invention, a first structural unit is attached to a solid substrate in a first fluidic flow. A second structural unit is attached to the first structural unit in a second fluidic flow, a third structural unit is attached to the second structural unit in a third fluidic flow, and so on, until a target structure comprising the structural units is assembled. The first, second, third and so on fluidic flows are separate and occur in order in a temporal sequence. The assembled target structure is removed from the solid substrate. During the temporal sequence, a specific attachment permutation is used repeatedly, in separate fluidic flows which occur at different times, to form multiple attachments between structural units in an assembly sequence.

Alternately, in some implementations of this invention, a second structural unit is attached to a first structural unit in a first fluidic flow, a third structural unit is attached to the second structural unit in a second fluidic flow, and so on, until a target structure comprising the structural units is assembled. The first, second, and so on fluidic flows are separate and occur in order in a temporal sequence. During the temporal sequence, a specific attachment permutation is used repeatedly, in separate fluidic flows which occur at different times, to form multiple attachments between structural units in an assembly sequence.

Definitions and Clarifications:

Here are a few definitions and clarifications. As used herein:

The terms "a", "an", and "another", when modifying a noun, do not imply that only one of the noun exists. For example, if there is "a" growth chamber, there may be multiple growth chambers. Or, if there is "another" brick, there may, in addition, be even more bricks.

The terms "affix", "attach", "join", and "connect", and all terms with similar meaning, shall be construed broadly, in each case as if preceded by the words "directly or indirectly". Likewise, the terms "between" and "among" shall be construed broadly. For example, the terms "between" and "among" include directly or indirectly between, or directly or indirectly among. Consider an example in which items A, B, C, D, E are arranged in a straight line. In that example, an attachment, connection or joint may be "between" A and E even though the connection is indirect and the joint directly connects A to B, B to C, C to D, and D to E. Furthermore, in that example, item C is "between" items A and E—even though D intervenes between C and E; and B intervenes between A and C.

An "assembly sequence" is a sequence of bricks. An assembly sequence is two or more bricks long. For example, an assembly sequence may be hundreds of bricks long, and may branch and link with other assembly sequences.

An "attachment permutation" is a permutation of n nucleobases, where n is the number of nucleobases in an attachment site on one brick that participate in base pairing to form an attachment with another brick. For example, if a specific attachment permutation is used to form multiple attachments, then in each of those multiple attachments, the base pairs are arranged in the same ordered sequence.

The term "base pair" shall be construed broadly. For example, the term "base pair" includes both naturally occurring base pairs and unnatural base pairs. For example, the term "base pair" includes naturally occurring adenine-thymine, cytosine-guanine, and adenine-uracil pairs. Also, for example, the term "base pair" includes (a) unnatural base pairs invented by Eric Kool and his colleagues, including the Z-F and Q-F pairs; (b) unnatural base pairs invented by Steven Brenner and his colleagues, including the isoG-isoC, Z-F, V-J, K-X, and S-B pairs; and (c) unnatural base pairs invented by Ichiro Hirao and his colleagues, including the x-y, s-x, Ds-Pa, and Ds-Px base pairs. Also, for example, the term "base pair" includes a base pair in which at least one of the bases is unnatural.

The term "base pairing" shall be construed broadly to mean any linking between two bases of a base pair. For example, "base pairing" may occur between two nucleobases within a single DNA molecule, the first of which is on one strand of the molecule's double helix and the second of which is on the other strand of the double helix. Or, for example, "base pairing" may occur between nucleobases on different double helices (e.g., in a Holliday junction). Or, for example, "base pairing" may occur between a nucleobase that is part of a DNA strand and a nucleobase that is anchored to something else chemically.

A "brick" is a structural unit. A brick may be of any shape or size. The main body of a brick may be of any material composition.

The term "comprise" (and grammatical variations thereof) shall be construed broadly, as if followed by "without limitation". If A comprises B, then A includes B and may include other things.

The term "e.g." means for example.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that mentions "a first" thing and "a second" thing is simply a way of identifying the two things, respectively, so that they each can be referred to later with specificity (e.g., by referring to "the first" thing and "the second" thing); (2) such a phrase does not imply an order of the two things; (3) such a phrase does not imply that there are only two of the things; (4) such a phrase does not imply that no other thing preceded the first thing, or that no other thing intervenes between, overlaps with, or follows the two things, (5) a "first" listed step in a sequence of steps may be proceeded by an unlisted step; and (6) a step that is not listed may overlap with or intervene between a "first" and a "second" step. However, if such a phrase expressly says that steps occur "in order", then the "first" thing occurs before the "second", and unless the context clearly indicates otherwise, clauses (3), (4), (5) and (6) of the immediately preceding sentence continue to apply. A phrase that mentions "a third" thing, a "fourth" thing and so on shall be construed in like manner.

The terms "horizontal" and "vertical" shall be construed broadly. For example, "horizontal" and "vertical" may refer to two arbitrarily chosen coordinate axes in a Euclidian two dimensional space.

The term "include" (and grammatical variations thereof) shall be construed broadly, as if followed by "without limitation".

A thing (e.g., a method, process, apparatus, article of manufacture, system, machine, device, or technology) is "Known" if (and only if) the thing would be known to a person of ordinary skill in the art to which it pertains, or with which it is most nearly connected, as of the priority date of this patent application.

A synthesized compound is "naturally occurring" compound if the compound also occurs naturally without synthesis.

The term "nucleobase" shall be construed broadly. For example, the term "nucleobase" includes one of the two parts of an unnatural base pair.

The term "or" is inclusive, not exclusive. For example "A or B" is true if A is true, or B is true, or both A or B are true. Also, for example, a calculation of "A or B" means a calculation of A, or a calculation of B, or a calculation of A and B.

A parenthesis is simply to make text easier to read, by indicating a grouping of words. A parenthesis does not mean that the parenthetical material is optional or can be ignored.

Notwithstanding anything to the contrary herein, the term "tangible machine-readable media" does not include any transitory, propagating signal. For example, "tangible machine-readable media" does not include (a) any electromagnetic wave or impulse; and (b) any mechanical wave or impulse.

"3D" means three-dimensional.

"Unnatural" means not occurring in nature. For example, a synthesized compound is unnatural if it does not occur in nature.

Grammatical variations of defined terms shall be construed in like manner as the defined terms. For example, if a verb is defined in one conjugation, then other conjugations of that verb shall be construed in like manner. Or, for example, if a noun is defined in one declension, then other declensions of that noun shall be construed in like manner. Or for example, the noun "attachment" shall be construed in like manner as the defined verb "attach".

Variations:

This invention may be implemented in many different ways. Here are some non-limiting examples.

This invention may be implemented as a method comprising the following steps, in combination: (a) attaching a first structural unit to a solid substrate in a first fluidic flow; (b) attaching a second structural unit to the first structural unit in a second fluidic flow, attaching a third structural unit to the second structural unit in a third fluidic flow, and so on, until a target structure comprising the structural units is assembled, the first, second, third and so on fluidic flows being separate and occurring in order in a temporal sequence; and (c) removing the target structure from the solid substrate; wherein (i) attachments between structural units are formed by nucleobase pairing, and (ii) during the temporal sequence, a specific attachment permutation is used repeatedly, in separate fluidic flows which occur at different times, to form multiple attachments between structural units in an assembly sequence. Furthermore: (1) the target structure, when assembled, may include a physical sequence of structural units; the overall direction of the physical sequence may vary as a function of position; and a majority of the changes of the overall direction may consist of 90 degree turns; (2) each attachment site on a structural unit may comprise three elongated structures that are encoded with nucleobases for selective docking with other structural units; (3) a payload may be attached to or confined in the target structure, which payload does not consist of the structural units; (4) attachment between structural units may occur at or adjacent to attachment sites on the structural units; and a structural unit may include exactly four attachment sites; (5) one or more attachments between structural units may be dynamically reconfigurable; (6) nucleic acid strand displacement may be employed to activate attachment sites; (7) one or more nucleobases used in the nucleobase pairing may be unnatural; (8) sensor measurements may be used to assess yield or other metrics of an assembly step; (9) microscopy imaging of fluorescence from FRET fluorophores may be used to assess yield or other metrics of an assembly step; (10) light, or lack thereof, from three different fluorophore pairs may be indicative of whether an assembly step yielded a right turn, left turn, go straight, or no connection; (11) a structural unit may have a main body; and the overall shape of an external planar face of the main body, not including any elongated protrusions from the main body, may be a parallelogram; (12) when the target structure is assembled, a plurality of structural units may be connected in-plane.

This invention may be implemented as a system comprising, in combination: (a) a microfluidic growth chamber; (b) one or more valves configured for controlling movement of fluid to the growth chamber, including materials suspended, positioned or dissolved in the fluid; (c) tangible machine-readable media; and (d) one or more processors; wherein (i) the tangible machine-readable media encode instructions for the one or more processors to control an assembly process, which assembly process occurs in the growth chamber and comprises attaching a second structural unit to a first structural unit in a first fluidic flow, attaching a third structural unit to the second structural unit in a second fluidic flow, and so on, until a target structure comprising the structural units is assembled, wherein the first, second, and so on fluidic flows are separate and occur in order in a temporal sequence, (ii) attachments between structural units are formed by nucleobase pairing, and (iii) during the temporal sequence, a specific attachment permutation is used repeatedly, in separate fluidic flows which occur at different times, to form multiple attachments between structural units in an assembly sequence. Furthermore: (1) a microscopy imager for measuring fluorescence from FRET fluorophores may be used to assess yield or other metrics of an assembly step; (2) the target structure, when assembled, may include a physical sequence of structural units; overall direction of the physical sequence may vary as a function of position; and one or more changes of the overall direction may consist of 108 degree turns; and (3) each attachment site on a structural unit may comprise three elongated structures that are encoded with nucleobases for selective docking with other structural units.

This invention may be implemented as an article of manufacture comprising a plurality of structural units, wherein: (a) each of the structural units, respectively, includes a main body and two or more attachment sites, each of the attachment sites comprising three elongated structures that protrude from the main body; (b) attachments between structural units are formed by nucleobase pairing; and (c) for each respective nucleobase pair participating in the nucleobase pairing that joins structural units, one nucleobase in the respective pair is part of a first attachment site of a first structural unit and the other nucleobase in the respective pair is part of a second attachment site in a second structural unit or is positioned between the first and second attachment sites. Furthermore: (1) the article of manufacture may attach to, or confine, a payload; and (2) the article of manufacture may include the payload.

Conclusion:

While exemplary implementations are disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention. Numerous modifications may be made by one of ordinary skill in the art without departing from the scope of the invention.

What is claimed is:

1. A method comprising the following steps, in combination:
   (a) attaching a first deoxyribonucleic acid (DNA) brick to a solid substrate in a first fluidic flow;
   (b) attaching a second DNA brick to the first DNA brick in a second fluidic flow;
   (c) then attaching, to a previous DNA brick, an additional DNA brick in an additional fluidic flow,
   (d) then repeating step (c) at least one more time; and
   (e) removing a structure from the solid substrate, which structure comprises the DNA bricks attached to each other in steps (b), (c) and (d);
   wherein
   (i) the previous DNA brick mentioned in step (c) is (I) in the first iteration of step (c), the second DNA brick, and (II) in each subsequent iteration of step (c) pursuant to step (d), the additional DNA brick attached in the previous iteration of step (c),
   (ii) the fluidic flows are separate from each other and occur in order in a temporal sequence,
   (iii) attachments between structural units comprise nucleobase pairing, and
   (iv) during the temporal sequence, a specific attachment permutation is used repeatedly, in separate fluidic flows which occur at different times, to form multiple attachments between structural units in an assembly sequence.

2. The method of claim 1, wherein:
   (a) the target structure, when assembled, includes a physical sequence of DNA bricks; and
   (b) overall direction of the physical sequence varies as a function of position; and
   (c) a majority of the changes of the overall direction consist of 90 degree turns, each 90 degree turn being a 90 degree angle between long axes of adjacent structural units.

3. The method of claim 1, wherein each attachment site on a DNA brick comprises three elongated structures that comprise nucleobases for selective docking with other structural units.

4. The method of claim 3, further comprising the step of attaching or confining a payload to or in the target structure, which payload does not consist of the structural units.

5. The method of claim 1, wherein:
   (a) attachment between DNA bricks occurs at attachment sites on the structural units; and
   (b) a DNA brick includes exactly four attachment sites.

6. The method of claim 1, wherein DNA strand displacement reconfigures one or more attachments between structural units.

7. The method of claim 1, wherein toehold-mediated activation activates attachment sites.

8. The method of claim 1, wherein one or more nucleobases used in the nucleobase pairing are unnatural.

9. The method of claim 1, wherein sensor measurements assess yield or other metrics of an assembly step.

10. The method of claim 1, further comprising using microscopy imaging of fluorescence from FRET fluorophores to determine, based on light or lack thereof from three distinct fluorophore pairs, whether an assembly step yielded a right turn, left turn, go straight, or no connection.

11. The method of claim 1, wherein:
    (a) a DNA brick has a main body; and
    (b) overall shape of an external planar face of the main body, not including any elongated protrusions from the main body, is a parallelogram.

12. The method of claim 1, wherein, when the target structure is assembled, a plurality of DNA bricks are connected in-plane.

13. The method of claim 1, wherein the target structure, when assembled, is configured to attach to, or confine, a payload.

* * * * *